(12) United States Patent
Stice et al.

(10) Patent No.: US 6,235,969 B1
(45) Date of Patent: *May 22, 2001

(54) CLONING PIGS USING DONOR NUCLEI FROM NON-QUIESCENT DIFFERENTIATED CELLS

(75) Inventors: Steven L. Stice; James M. Robl, both of Belchertown; Jose Cibelli, Amherst; Paul Golueke, Belchertown, all of MA (US)

(73) Assignee: University of Massachusetts, Amherst, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/888,057

(22) Filed: Jul. 3, 1997

Related U.S. Application Data

(63) Continuation-in-part of application No. 08/781,752, filed on Jan. 10, 1997, now Pat. No. 5,945,577.

(51) Int. Cl.⁷ .................................................... C12N 15/00
(52) U.S. Cl. ................................................. 800/24; 800/17
(58) Field of Search ................................... 800/24, 17, 8

(56) References Cited

U.S. PATENT DOCUMENTS

| | | | |
|---|---|---|---|
| 4,994,384 | * 2/1991 | Pather et al. | 800/24 |
| 5,057,420 | * 10/1991 | Massey | 800/24 |
| 6,147,276 | * 11/2000 | Campbell et al. | 800/24 |

FOREIGN PATENT DOCUMENTS

| | | |
|---|---|---|
| WO 91/13150 | 9/1991 | (WO) . |
| WO 94/29442 | 12/1994 | (WO) . |
| WO 95/16770 | * 6/1995 | (WO) . |
| WO 95/17500 | * 6/1995 | (WO) . |
| WO 95/34696 | * 12/1995 | (WO) . |
| WO 96/07732 | * 3/1996 | (WO) . |
| WO 97/07668 | * 3/1997 | (WO) . |
| WO 97/07669 | * 3/1997 | (WO) . |
| WO 97/37009 | * 10/1997 | (WO) . |

OTHER PUBLICATIONS

Theriogenology, vol. 45, No. 1, p. 287, XP000605648.*
Journal of Reproduction and Fertility Supplement, vol. 5, Jan. 1995, p. 60, P000607293.*
Molecular Reproduction and Development, vol. 38, No. 3, Jul. 1994, pp. 264–267, XP002067033.*
Theriogenology, vol. 47, No. 1, p. 241, XP002067034.*
Nature, vol. 385, No. 6619, pp. 810–813, XP002067035.*
Science, vol. 278, No. 5346, pp. 2130–2133, XP02067036.*
Biology of Reproduction, vol. 57, No. 2, pp. 385–393, XP002067037.*
Journal of Neurochemistry, vol. 70, No. suppl. 1, p. S46, XP002067038.*
Theriogenology, vol. 49, No. 1, pp. 129–138, XP002067444.*
Sims et al. (1993) Proc. Natl. Acad. Sci. 90, 6143–6147.*
Kono et al (1995) Expt. Cell Res. 221, 478–485.*
Lovell–Badge et al Cold Spring Harbor Symp. Quant. Biol. (1985), 50 (Mol. Biol. Devel.), Cold Spring Harbor Lab. Press, Cold Spring Harbor, NY, pp. 707–711.*
Wilmut et al (1997) Nature 385, 810–813.*
Campbell et al (1996) Nature 380, 64–66.*
Schultz et al (1995) Sem. Cell Biol. 6, 201–208.*
Hyttinen et al (1994) Bioltechnology 12, 606–608.*
Sims et al (1993) Proced. Natl. Acad. Sci. 90, 6143–6147.*
Schultz et al (1995) Seminars in Cell Biology 6, 201–208.*
Kappell et al (1992) Current Opinion in Biotechnology 3, 548–553.*
Wall (1996) Theriogenology 45, 57–68.*
Houdebine (1994) Journal of Biotechnology 34, 269–287.*
Mullins et al (1996) Journal of Clinical Investigation 98, S37–S40.*
Seamark (1994) Reproductive Fertility and Development 6, 653–657.*
Cisneros et al (1996) J. Animal Science 74, 925–933.*
Cukrowska et al (1996) Immunology 87, 487–492.*
Fodor et al (1994) Proced. Natl. Acad. Sci. 91, 11153–11157.*
Strojek et al 1990) Threiogenology 33, 901–913.*
Brameld et al (1995) J. Endocrin. 146, 239–245.*
Onishi et al (1994) Biology of Reproduction 51, 1069–1075.*
Rosengard et al (1995) Transplantation 59, 1325–1333.*
First et al, Systems for Production of Calves from Cultured Bovine Embryonic Cells, *Reproduction, Fertility, and Development*, vol. 6, pp 553–562 (1994).
Bartlett et al, Evaluation of extracellular matrices and the plasminogen activator system in sheep inner cell mass and trophectodermal outgrowth in vitro, *Biology of Reproduction*, vol. 52, pp 1426–1445 (1995).
Talbot et al, In vitro pluripotency of epiblasts derived from bovine blastocysts, *Molecular Reproduction and Development*, vol. 42, pp 35–52 (1995).
Talbot et al, Culturing the epiblast cells of the pig blastocyst. *In Vitro Cellular and Development Biology*, vol. 29A, pp. 543–554 (Jul. 1993).
Annelies et al, Isolation and Characterization of Permanent Cell Lines from Inner Cell Mass Cells of Bovine Blastocyst, *Molecular Reproduction and Development*, vol. 40, pp 444–454 (1995).

(List continued on next page.)

Primary Examiner—Deborah Grouch
(74) Attorney, Agent, or Firm—Robin L. Teskin

(57) ABSTRACT

An improved method of nuclear transfer involving the transplantation of donor differentiated pig cell nuclei into enucleated pig oocytes is provided. The resultant nuclear transfer units are useful for multiplication of genotypes and transgenic genotypes by the production of fetuses and offspring. Production of genetically engineered or transgenic pig embryos, fetuses and offspring is facilitated by the present method since the differentiated cell source of the donor nuclei can be genetically modified and clonally propagated.

26 Claims, No Drawings

OTHER PUBLICATIONS

Collas et al, Nuclear Transplantation by Microinjection of Inner Cell Mass and Granulosa Cell Nuclei, *Molecular Reproduction and Development*, vol. 38, pp. 264–267 (1994).

Sims et al, Production of calves by transfer of nuclei from cultured inner cell mass cells, *Proceedings of the National Academy of Sciences*, USA, vol. 90, pp 6143–6147 (Jun. 1993).

Callard, R. et al., (1994), *The Cytokine Facts Book*, Academic Press, pp. 163–167.

Talbot et al., (1993), In vitro *Cellular and Development Biology* 29A, pp. 543–554.

Seamark et al., (1994), *Reproduction Fertility and Development* 6, pp. 653–657.

Bradley et al., (1992), *BioTechnology* 10, pp. 543–539.

Kappel et al. (1992), *Current Opinion in Biotechnology* 3, pp. 548–553.

Sims et al., (1994) *Proc. Natl. Acad. Sci USA 91*, pp. 6143–6147.

Stice et al., "Pluripotent Embryonic Cell Lines Direct Embryonic Development Following Nuclear Transfer", *Biology of Reproduction*, vol. 54, No. 1 Jan. 1996, pp. 100–110.

Cibelli J.B. et al., "Production of germline chimeric bovine fetuses from transgenic enbryonic stem cells", *Theriogenology*, vol. 47, No. 1, Jan. 1997, p. 241.

\* cited by examiner

CLONING PIGS USING DONOR NUCLEI FROM NON-QUIESCENT DIFFERENTIATED CELLS

This application is a continuation-in-part of Ser. No. 08/781,752, now U.S. Pat. No. 5,945,977 issued Aug. 31, 1999 the contents of which are hereby incorporated by reference.

FIELD OF THE INVENTION

The present invention relates to cloning procedures in which cell nuclei derived from differentiated pig cells are transplanted into enucleated mammalian oocytes of the same species as the donor nuclei. The nuclei are reprogrammed to direct the development of cloned embryos, which can then be transferred into recipient females to produce fetuses and offspring, or used to produce cultured inner cell mass cells (CICM). The cloned embryos can also be combined with fertilized embryos to produce chimeric embryos, fetuses and/or offspring.

BACKGROUND OF THE INVENTION

The use of ungulate inner cell mass (ICM) cells for nuclear transplantation has also been reported. For example, Collas et al., *Mol. Reprod. Dev.*, 38:264–267 (1994) discloses nuclear transplantation of bovine ICMs by microinjection of the lysed donor cells into enucleated mature oocytes. Collas et al. disclosed culturing of embryos in vitro for seven days to produce fifteen blastocysts which, upon transferral into bovine recipients, resulted in four pregnancies and two births. Also, Keefer et al., *Biol. Reprod.*, 50:935–939 (1994), disclosed the use of bovine ICM cells as donor nuclei in nuclear transfer procedures, to produce blastocysts which, upon transplantation into bovine recipients, resulted in several live offspring. Further, Sims et al., *Proc. Natl. Acad. Sci., USA*, 90:6143–6147 (1993), disclosed the production of calves by transfer of nuclei from short-term in vitro cultured bovine ICM cells into enucleated mature oocytes.

The production of live lambs following nuclear transfer of cultured embryonic disc cells has also been reported (Campbell et al., *Nature*, 380:64–68 (1996)). Still further, the use of bovine pluripotent embryonic cells in nuclear transfer and the production of chimeric fetuses has been reported (Stice et al., *Biol. Reprod.*, 54:100–110 (1996); Collas et al, *Mol. Reprod. Dev.*, 38:264–267 (1994)). Collas et al demonstrated that granulosa cells (adult cells) could be used in a bovine cloning procedure to produce embryos. However, there was no demonstration of development past early embryonic stages (blastocyst stage). Also, granulosa cells are not easily cultured and are only obtainable from females. Collas et al did not attempt to propagate the granulosa cells in culture or try to genetically modify those cells. Wilmut et al (*Nature*, 365:810–813 (1997)) produced nuclear transfer sheep offspring derived from fetal fibroblast cells, and one offspring from a cell derived from an adult sheep.

Cloning pig cells is more difficult in comparison with cells of other species. This phenomenon is illustrated by the following table:

| SPECIES (from hardest to easiest to clone) | CELL TYPE CLONED | OFFSPRING PRODUCED |
|---|---|---|
| Pig (Prather, 1989) | 2 and 4 cell stage embryo | yes |
| Pig (Prather, 1989; Liu et al., 1995) | greater than 4 cell stage | no |
| Mouse (Cheong et al., 1993) | 2, 4 and 8 cell stage embryo | yes |
| Mouse (Tsunoda et al., 1993) | greater than 8 cell stage | no |
| Cattle (Keefer et al., 1994) | 64 to 128 cell stage (ICM) | yes |
| Cattle (Stice et al., 1996) | embryonic cell line from ICM | no |
| Sheep (Smith et al., 1989) | 64 to 128 cell stage (ICM) | yes |
| Sheep (Campbell et al., 1996) | embryonic cell line from ICM | yes |
| Sheep (Wilmut et al., 1997) | fetal and adult cells | yes |

There also exist problems in the area of producing transgenic pigs. By current methods, heterologous DNA is introduced into either early embryos or embryonic cell lines that differentiate into various cell types in the fetus and eventually develop into a transgenic animal. However, many early embryos are required to produce one transgenic animal and, thus, this procedure is very inefficient. Also, there is no simple and efficient method of selecting for a transgenic embryo before going through the time and expense of putting the embryos into surrogate females. In addition, gene targeting techniques cannot be easily accomplished with early embryo transgenic procedures.

Embryonic stem cells in mice have enabled researchers to select for transgenic cells and perform gene targeting. This allows more genetic engineering than is possible with other transgenic techniques. However, embryonic stem cell lines and other embryonic cell lines must be maintained in an undifferentiated state that requires feeder layers and/or the addition of cytokines to media. Even if these precautions are followed, these cells often undergo spontaneous differentiation and cannot be used to produce transgenic offspring by currently available methods. Also, some embryonic cell lines have to be propagated in a way that is not conducive to gene targeting procedures.

Methods for deriving embryonic stem (ES) cell lines in vitro from early preimplantation mouse embryos are well known. (See, e.g., Evans et al., *Nature*, 29:154–156 (1981); Martin, *Proc. Natl. Acad. Sci., USA*, 78:7634–7638 (1981)). ES cells can be passaged in an undifferentiated state, provided that a feeder layer of fibroblast cells (Evans et al., Id.) or a differentiation inhibiting source (Smith et al., *Dev. Biol.*, 121:1–9 (1987)) is present.

ES cells have been previously reported to possess numerous applications. For example, it has been reported that ES cells can be used as an in vitro model for differentiation, especially for the study of genes which are involved in the regulation of early development. Mouse ES cells can give rise to germline chimeras when introduced into preimplantation mouse embryos, thus demonstrating their pluripotency (Bradley et al., *Nature*, 309:255–256 (1984)).

In view of their ability to transfer their genome to the next generation, ES cells have potential utility for germline manipulation of livestock animals by using ES cells with or without a desired genetic modification. Moreover, in the case of livestock animals, e.g., ungulates, nuclei from like preimplantation livestock embryos support the development of enucleated oocytes to term (Smith et al., *Biol. Reprod.,* 40:1027–1035 (1989); and Keefer et al., *Biol. Reprod.,* 50:935–939 (1994)). This is in contrast to nuclei from mouse embryos which beyond the eight-cell stage after transfer reportedly do not support the development of enucleated oocytes (Cheong et al, *Biol. Reprod.,* 48:958 (1993)). Therefore, ES cells from livestock animals are highly desirable because they may provide a potential source of totipotent donor nuclei, genetically manipulated or otherwise, for nuclear transfer procedures.

Some research groups have reported the isolation of purportedly pluripotent embryonic cell lines. For example, Notarianni et al., *J. Reprod. Fert. Suppl.,* 43:255–260 (1991), reports the establishment of purportedly stable, pluripotent cell lines from pig and sheep blastocysts which exhibit some morphological and growth characteristics similar to that of cells in primary cultures of inner cell masses isolated immunosurgically from sheep blastocysts. Also, Notarianni et al., *J. Reprod. Fert. Suppl.,* 41:51–56 (1990) discloses maintenance and differentiation in culture of putative pluripotential embryonic cell lines from pig blastocysts. Gerfen et al., *Anim. Biotech,* 6(1):1–14 (1995) discloses the isolation of embryonic cell lines from porcine blastocysts. These cells are stably maintained in mouse embryonic fibroblast feeder layers without the use of conditioned medium, and reportedly differentiate into several different cell types during culture.

Further, Saito et al., *Roux's Arch. Dev. Biol.,* 201:134–141 (1992) reports cultured, bovine embryonic stem cell-like cell lines which survived three passages, but were lost after the fourth passage. Handyside et al., *Roux's Arch. Dev. Biol.,* 196:185–190 (1987) discloses culturing of immunosurgically isolated inner cell masses of sheep embryos under conditions which allow for the isolation of mouse ES cell lines derived from mouse ICMs. Handyside et al. reports that under such conditions, the sheep ICMs attach, spread, and develop areas of both ES cell-like and endoderm-like cells, but that after prolonged culture only endoderm-like cells are evident.

Recently, Cherny et al., *Theriogenology,* 41:175 (1994) reported purportedly pluripotent bovine primordial germ cell-derived cell lines maintained in long-term culture. These cells, after approximately seven days in culture, produced ES-like colonies which stained positive for alkaline phosphatase (AP), exhibited the ability to form embryoid bodies, and spontaneously differentiated into at least two different cell types. These cells also reportedly expressed mRNA for the transcription factors OCT4, OCT6 and HES1, a pattern of homeobox genes which is believed to be expressed by ES cells exclusively.

Also recently, Campbell et al., *Nature,* 380:64–68 (1996) reported the production of live lambs following nuclear transfer of cultured embryonic disc (ED) cells from day nine ovine embryos cultured under conditions which promote the isolation of ES cell lines in the mouse. The authors concluded that ED cells from day nine ovine embryos are totipotent by nuclear transfer and that totipotency is maintained in culture.

Van Stekelenburg-Hamers et al., *Mol. Reprod. Dev.,* 40:444–454 (1995), reported the isolation and characterization of purportedly permanent cell lines from inner cell mass cells of bovine blastocysts. The authors isolated and cultured ICMs from 8 or 9 day bovine blastocysts under different conditions to determine which feeder cells and culture media are most efficient in supporting the attachment and outgrowth of bovine ICM cells. They concluded that the attachment and outgrowth of cultured ICM cells is enhanced by the use of STO (mouse fibroblast) feeder cells (instead of bovine uterus epithelial cells) and by the use of charcoal-stripped serum (rather than normal serum) to supplement the culture medium. Van Stekelenburg et al reported, however, that their cell lines resembled epithelial cells more than pluripotent ICM cells.

Smith et al., WO 94/24274, published Oct. 27, 1994, Evans et al, WO 90/03432, published Apr. 5, 1990, and Wheeler et al, WO 94/26889, published Nov. 24, 1994, report the isolation, selection and propagation of animal stem cells which purportedly may be used to obtain transgenic animals. Evans et al. also reported the derivation of purportedly pluripotent embryonic stem cells from porcine and bovine species which assertedly are useful for the production of transgenic animals. Further, Wheeler et al, WO 94/26884, published Nov. 24, 1994, disclosed embryonic stem cells which are assertedly useful for the manufacture of chimeric and transgenic ungulates.

Thus, based on the foregoing, it is evident that many groups have attempted to produce ES cell lines, e.g., because of their potential application in the production of cloned or transgenic embryos and in nuclear transplantation.

Therefore, notwithstanding what has previously been reported in the literature, there exists a need for improved methods of cloning pigs using cultured differentiated cells as donor nuclei.

OBJECTS AND SUMMARY OF THE INVENTION

It is an object of the invention to provide novel and improved methods for producing cloned pigs using cultured differentiated cells as donor nuclei.

It is a more specific object of the invention to provide a novel method for cloning pigs which involves transplantation of the nucleus of a differentiated pig cell into an enucleated pig oocyte.

It is another object of the invention to provide a method for multiplying adult pigs having proven genetic superiority or other desirable traits.

It is another object of the invention to provide an improved method for producing genetically engineered or transgenic pigs (i.e., NT units, fetuses, offspring). The invention also provides genetically engineered or transgenic pigs, including those made by such a method.

It is a more specific object of the invention to provide a method for producing genetically engineered or transgenic pigs by which a desired DNA sequence is inserted, removed or modified in a differentiated pig cell or cell nucleus prior to use of that differentiated cell or cell nucleus for formation of a NT unit. The invention also provides genetically engineered or transgenic pigs made by such a method.

It is another object of the invention to provide a novel method for producing pig CICM cells which involves transplantation of a nucleus of a differentiated pig cell into an enucleated pig oocyte, and then using the resulting NT unit to produce CICM cells. The invention also provides pig CICM cells produced by such a method.

It is another object of the invention to use such pig CICM cells for therapy or diagnosis.

It is a specific object of the invention to use such pig CICM cells for treatment or diagnosis of any disease wherein cell, tissue or organ transplantation is therapeutically or diagnostically beneficial. The CICM cells may be used within the same species or across species.

It is another object of the invention to use cells or tissues derived from pig NT units, fetuses or offspring for treatment or diagnosis of any disease wherein cell, tissue or organ transplantation is therapeutically or diagnostically beneficial. Such diseases and injuries include Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases. The tissues may be used within the same species or across species.

It is another specific object of the invention to use cells or tissues derived from pig NT units, fetuses or offspring, or pig CICM cells produced according to the invention for the production of differentiated cells, tissues or organs.

It is another specific object of the invention to use cells or tissues derived from pig NT units, fetuses or offspring, or pig CICM cells produced according to the invention in vitro, e.g. for study of cell differentiation and for assay purposes, e.g. for drug studies.

It is another object of the invention to use cells, tissues or organs produced from such tissues derived from pig NT units, fetuses or offspring, or pig CICM cells to provide improved methods of transplantation therapy. Such therapies include by way of example treatment of diseases and injuries including Parkinson's, Huntington's, Alzheimer's, ALS, spinal cord injuries, multiple sclerosis, muscular dystrophy, diabetes, liver diseases, heart disease, cartilage replacement, burns, vascular diseases, urinary tract diseases, as well as for the treatment of immune defects, bone marrow transplantation, cancer, among other diseases.

It is another object of the invention to provide genetically engineered or transgenic tissues derived from pig NT units, fetuses or offspring, or pig CICM cells produced by inserting, removing or modifying a desired DNA sequence in a differentiated pig cell or cell nucleus prior to use of that differentiated cell or cell nucleus for formation of a NT unit.

It is another object of the invention to use the transgenic or genetically engineered tissues derived from pig NT units, fetuses or offspring, or pig CICM cells produced according to the invention for gene therapy, in particular for the treatment and/or prevention of the diseases and injuries identified, supra.

It is another object of the invention to use the tissues derived from pig NT units, fetuses or offspring, or pig CICM cells produced according to the invention, or transgenic or genetically engineered tissues derived from pig NT units, fetuses or offspring, or pig CICM cells produced according to the invention as nuclear donors for nuclear transplantation.

It is another object of the invention to use transgenic or genetically engineered pig offspring produced according to the invention in order to produce pharmacologically important proteins.

Thus, in one aspect, the present invention provides a method for cloning a pig (e.g., embryos, fetuses, offspring). The method comprises:
  (i) inserting a desired differentiated pig cell or cell nucleus into an enucleated pig oocyte, under conditions suitable for the formation of a nuclear transfer (NT) unit;
  (ii) activating the resultant nuclear transfer unit; and
  (iii) transferring said cultured NT unit to a host pig such that the NT unit develops into a fetus.

Optionally, the activated nuclear transfer unit is cultured until greater than the 2-cell developmental stage.

The cells, tissues and/or organs of the fetus are advantageously used in the area of cell, tissue and/or organ transplantation, or production of desirable genotypes.

The present invention also includes a method of cloning a genetically engineered or transgenic pig, by which a desired DNA sequence is inserted, removed or modified in the differentiated pig cell or cell nucleus prior to insertion of the differentiated pig cell or cell nucleus into the enucleated oocyte. Genetically engingeered or transgenic pigs produced by such a method are advantageously used in the area of cell, tissue and/or organ transplantation, production of desirable genotypes, and production of pharmaceutical proteins.

Also provided by the present invention are pigs obtained according to the above method, and offspring of those pigs.

In another aspect, the present invention provides a method for producing pig CICM cells. The method comprises:
  (i) inserting a desired differentiated pig cell or cell nucleus into an enucleated pig oocyte, under conditions suitable for the formation of a nuclear transfer (NT) unit;
  (ii) activating the resultant nuclear transfer unit; and
  (iii) culturing cells obtained from said cultured NT unit to obtain pig CICM cells.

Optionally, the activated nuclear transfer unit is cultured until greater than the 2-cell developmental stage.

The pig CICM cells are advantageously used in the area of cell, tissue and organ transplantation.

With the foregoing and other objects, advantages and features of the invention that will become hereinafter apparent, the nature of the invention may be more clearly understood by reference to the following detailed description of the preferred embodiments of the invention and to the appended claims.

DETAILED DESCRIPTION OF THE INVENTION

The present invention provides improved procedures for cloning pigs by nuclear transfer or nuclear transplantation. In the subject application, nuclear transfer or nuclear transplantation or NT are used interchangeably.

According to the invention, cell nuclei derived from differentiated pig cells are transplanted into enucleated pig oocytes. The nuclei are reprogrammed to direct the development of cloned embryos, which can then be transferred into recipient females to produce fetuses and offspring, or used to produce CICM cells. The cloned embryos can also be combined with fertilized embryos to produce chimeric embryos, fetuses and/or offspring.

Prior art methods have used embryonic cell types in cloning procedures. This includes work by Campbell et al (*Nature*, 380:64–68, 1996) and Stice et al (*Biol. Reprod.,* 20 54:100–110, 1996). In both of those studies, embryonic cell lines were derived from embryos of less than 10 days of gestation. In both studies, the cells were maintained on a feeder layer to prevent overt differentiation of the donor cell to be used in the cloning procedure. The present invention uses differentiated cells.

Adult cells and fetal fibroblast cells from a sheep have purportedly been used to produce sheep offspring (Wilmut et al, 1997). Studies have shown, however, that the cloning of pigs is more difficult than cloning sheep. In fact, of the mammalian species studied, cloning of sheep appears to be the easiest, and pig cloning appears to be the most difficult. The successful cloning of pigs using differentiated cell types according to the present invention was quite unexpected.

Thus, according to the present invention, multiplication of superior genotypes of pigs is possible. This will allow the multiplication of adult pigs with proven genetic superiority or other desirable traits. Genetic progress will be accelerated in the pig. By the present invention, there are potentially billions of fetal or adult pig cells that can be harvested and used in the cloning procedure. This will potentially result in many identical offspring in a short period.

There has also been speculation that the Wilmut et al method will lead to the generation of transgenic animals (see MacQuitty, *Nature Biotech.*, 15:294 (1997)). However, there is no reason to assume, for example, that nuclei from adult cells that have been transfected with exogenous DNA will be able to survive the process of nuclear transfer. In this regard, it is known that the properties of mouse embryonic stem (ES) cells are altered by in vitro manipulation such that their ability to form viable chimeric embryos is effected. Therefore, prior to the present invention, the cloning of transgenic animals could not have been predicted.

The present invention also allows simplification of transgenic procedures by working with a cell source that can be clonally propagated. This eliminates the need to maintain the cells in an undifferentiated state, thus, genetic modifications, both random integration and gene targeting, are more easily accomplished. Also by combining nuclear transfer with the ability to modify and select for these cells in vitro, this procedure is more efficient than previous transgenic embryo techniques. According to the present invention, these cells can be clonally propagated without cytokines, conditioned media and/or feeder layers, further simplifying and facilitating the transgenic procedure. When transfected cells are used in cloning procedures according to the invention, transgenic pig embryos are produced which can develop into fetuses and offspring. Also, these transgenic cloned embryos can be used to produce CICM cell lines or other embryonic cell lines. Therefore, the present invention eliminates the need to derive and maintain in vitro an undifferentiated cell line that is conducive to genetic engineering techniques.

The present invention can also be used to produce cloned pig fetuses, offspring or CICM cells which can be used, for example, in cell, tissue and organ transplantation. By taking a fetal or adult cell from a pig and using it in the cloning procedure a variety of cells, tissues and possibly organs can be obtained from cloned fetuses as they develop through organogenesis. Cells, tissues, and organs can be isolated from cloned offspring as well. This process can provide a source of "materials" for many medical and veterinary therapies including cell and gene therapy. If the cells are transferred back into the animal in which the cells were derived, then immunological rejection is averted. Also, because many cell types can be isolated from these clones, other methodologies such as hematopoietic chimerism can be used to avoid immunological rejection among animals of the same species as well as between species.

Thus, in one aspect, the present invention provides a method for cloning a pig. In general, the pig will be produced by a nuclear transfer process comprising the following steps:
   (i) obtaining desired differentiated pig cells to be used as a source of donor nuclei;
   (ii) obtaining oocytes from a pig;
   (iii) enucleating said oocytes;
   (iv) transferring the desired differentiated cell or cell nucleus into the enucleated oocyte, e.g., by fusion or injection, to form NT units;
   (v) activating the resultant NT unit; and
   (vii) transferring said cultured NT unit to a host pig such that the NT unit develops into a fetus.

Optionally, the activated nuclear transfer unit is cultured until greater than the 2-cell developmental stage.

The present invention also includes a method of cloning a genetically engineered or transgenic pig, by which a desired DNA sequence is inserted, removed or modified in the differentiated pig cell or cell nucleus prior to insertion of the differentiated pig cell or cell nucleus into the enucleated oocyte.

Also provided by the present invention are pigs obtained according to the above method, and offspring of those pigs.

In addition to the uses described above, the genetically engineered or transgenic pigs according to the invention can be used to produced a desired protein, such as a pharmacologically important protein. That desired protein can then be isolated from the milk or other fluids or tissues of the transgenic pig. Alternatively, the exogenous DNA sequence may confer an agriculturally useful trait to the transgenic pig, such as disease resistance, decreased body fat, increased lean meat product, improved feed conversion, or altered sex ratios in progeny.

The present invention further provides for the use of NT fetuses and NT and chimeric offspring in the area of cell, tissue and organ transplantation.

In another aspect, the present invention provides a method for producing pig CICM cells. The method comprises:
   (i) inserting a desired differentiated pig cell or cell nucleus into an enucleated pig oocyte, under conditions suitable for the formation of a nuclear transfer (NT) unit;
   (ii) activating the resultant nuclear transfer unit; and
   (iii) culturing cells obtained from said cultured NT unit to obtain pig CICM cells.

Optionally, the activated nuclear transfer unit is cultured until greater than the 2-cell developmental stage.

The pig CICM cells are advantageously used in the area of cell, tissue and organ transplantation, or in the production of fetuses or offspring, including transgenic fetuses or offspring.

As used herein, a fetus is the unborn young of a viviparous animal after it has taken form in the uterus. In pigs, the fetal stage occurs from 30 days after conception until birth. A mammal is an adult from birth until death.

Preferably, the NT units will be cultured to a size of at least 2 to 400 cells, preferably 4 to 128 cells, and most preferably to a size of at least about 50 cells.

Nuclear transfer techniques or nuclear transplantation techniques are known in the literature and are described in many of the references cited in the Background of the Invention. See, in particular, Campbell et al, *Theriogenology*, 43:181 (1995); Collas et al, *Mol. Report Dev.*, 38:264–267 (1994); Keefer et al, *Biol. Reprod.*, 50:935–939 (1994); Sims et al, *Proc. Natl. Acad. Sci., USA*, 90:6143–6147 (1993); WO 94/26884; WO 94/24274, and WO 90/03432, which are incorporated by reference in their entirety herein. Also, U.S. Pat. Nos. 4,944,384 and 5,057,420 describe procedures for bovine nuclear transplantation.

Differentiated refers to cells having a different character or function from the surrounding structures or from the cell of origin. Differentiated pig cells are those cells which are past the early embryonic stage. More particularly, the differentiated cells are those from at least past the embryonic disc stage (day 10 of bovine embryogenesis). The differentiated cells may be derived from ectoderm, mesoderm or endoderm.

Pig cells may be obtained by well known methods. Pig cells useful in the present invention include, by way of example, epithelial cells, neural cells, epidermal cells, keratinocytes, hematopoietic cells, melanocytes, chondrocytes, lymphocytes (B and T lymphocytes), erythrocytes, macrophages, monocytes, mononuclear cells, fibroblasts, cardiac muscle cells, and other muscle cells, etc. Moreover, the pig cells used for nuclear transfer may be obtained from different organs, e.g., skin, lung, pancreas, liver, stomach, intestine, heart, reproductive organs, bladder, kidney, urethra and other urinary organs, etc. These are just examples of suitable donor cells. Suitable donor cells, i.e., cells useful in the subject invention, may be obtained from any cell or organ of the body. This includes all somatic or germ cells.

Fibroblast cells are an ideal cell type because they can be obtained from developing fetuses and adult pigs in large quantities. Fibroblast cells are differentiated somewhat and, thus, were previously considered a poor cell type to use in cloning procedures. Importantly, these cells can be easily propagated in vitro with a rapid doubling time and can be clonally propagated for use in gene targeting procedures. Again the present invention is novel because differentiated cell types are used. The present invention is advantageous because the cells can be easily propagated, genetically modified and selected in vitro.

Methods for isolation of oocytes are well known in the art. Essentially, this will comprise isolating oocytes from the ovaries or reproductive tract of a pig. A readily available source of pig oocytes is slaughterhouse materials.

For the successful use of techniques such as genetic engineering, nuclear transfer and cloning, oocytes must generally be matured in vitro before these cells may be used as recipient cells for nuclear transfer, and before they can be fertilized by the sperm cell to develop into an embryo. This process generally requires collecting immature (prophase I) oocytes from pig ovaries, e.g., pig ovaries obtained at a slaughterhouse, and maturing the oocytes in a maturation medium prior to fertilization or enucleation until the oocyte attains the metaphase II stage, which in the case of pig oocytes generally occurs about 35–45 hours post-aspiration. For purposes of the present invention, this period of time is known as the "maturation period." As used herein for calculation of time periods, "aspiration" refers to aspiration of the immature oocyte from ovarian follicles.

Additionally, metaphase II stage oocytes, which have been matured in vivo have been successfully used in nuclear transfer techniques. For example, mature metaphase II oocytes have been collected surgically from either non-superovulated or superovulated cows or heifers 35 to 48 hours past the onset of estrus or past the injection of human chorionic gonadotropin (hCG) or similar hormone. Similar procedures can be used in pigs.

The stage of maturation of the oocyte at enucleation and nuclear transfer has been reported to be significant to the success of NT methods. (See e.g., Prather et al., *Differentiation*, 48, 1–8, 1991). In general, successful mammalian embryo cloning practices use the metaphase II stage oocyte as the recipient oocyte because at this stage it is believed that the oocyte can be or is sufficiently "activated" to treat the introduced nucleus as it does a fertilizing sperm. In domestic animals, the oocyte activation period generally ranges from about 16–52 hours, preferably about 35–45 hours post-aspiration.

For example, immature oocytes may be washed in maturation medium (MAT—see Table in the Examples). The oocytes are then placed in 1 to 2 mls of MAT and cultured for 22 hours in the presence of db-cAMP and hormones. The oocytes are washed again, followed by culturing in MAT without hormones for an additional 18 hours.

After a maturation period, which ranges from about 30 to 50 hours, and preferably about 40 hours, the oocytes will be enucleated. Prior to enucleation the oocytes will preferably be removed and placed in HECM (Seshagiri and Bavister, 1989) containing 1 milligram per milliliter of hyaluronidase prior to removal of cumulus cells. This may be effected by repeated pipetting through very fine bore pipettes or by vortexing briefly (about 3 minutes). The stripped oocytes are then screened for polar bodies, and the selected metaphase II oocytes, as determined by the presence of polar bodies, are then used for nuclear transfer. Enucleation follows.

Enucleation may be effected by known methods, such as described in U.S. Pat. No. 4,994,384 which is incorporated by reference herein. For example, metaphase II oocytes are either placed in HECM, optionally containing 7.5 micrograms per milliliter cytochalasin B (CB) and 0.15 M sucrose, for immediate enucleation, or may be placed in a suitable medium, for example an embryo culture medium such as NCSU 23 (see Table in the Examples) at 39° C. and 5% $CO_2$, and then enucleated later, preferably not more than 24 hours later, and more preferably immediately.

Enucleation may be accomplished microsurgically using a micropipette to remove the polar body and the adjacent cytoplasm. The oocytes are screened to identify those of which have been successfully enucleated. This screening may be effected by staining the oocytes with 1 microgram per milliliter 33342 Hoechst dye for 20 min in NCSU 23, and then viewing the oocytes under ultraviolet irradiation for less than 10 seconds. The oocytes that have been successfully enucleated can then be placed in a suitable culture medium, e.g., HECM and 0.15 M sucrose.

In the present invention, the recipient oocytes will preferably be enucleated at a time ranging from about 30 hours to about 50 hours after the initiation of in vitro maturation, more preferably from about 38 hours to about 42 hours after initiation of in vitro maturation, and most preferably about 40 hours after initiation of in vitro maturation.

A single pig cell will then be transferred into the perivitelline space of the enucleated oocyte used to produce the NT unit. The pig cell and the enucleated oocyte will be used to produce NT units according to methods known in the art. For example, the cells may be fused by electrofusion. Electrofusion is accomplished by providing a pulse of electricity that is sufficient to cause a transient breakdown of the plasma membrane. This breakdown of the plasma membrane is very short because the membrane reforms rapidly. Thus, if two adjacent membranes are induced to breakdown and upon reformation the lipid bilayers intermingle, small channels will open between the two cells. Due to the thermodynamic instability of such a small opening, it enlarges until the two cells become one. Reference is made to U.S. Pat. No. 4,997,384 by Prather et al., (incorporated by reference in its entirety herein) for a further discussion of this process. A variety of electrofusion media can be used including e.g., sucrose, mannitol, sorbitol and phosphate buffered solution. Fusion can also be accomplished using Sendai virus as a fusogenic agent (Graham, Wister Inot. Symp. Monogr., Sep., 19, 1969). A preferred fusion medium is 0.28 M mannitol, 10 $\mu$M $CaCl_2$, 100 $\mu$M $MgSO_4$ and 10 mM histidine, pH 7.0.

Also, in some cases (e.g. with small donor nuclei) it may be preferable to inject the nucleus directly into the oocyte rather than using electroporation fusion. Such techniques are disclosed in Collas and Barnes, *Mol. Reprod. Dev.*, 38:264–267 (1994), incorporated by reference in its entirety herein.

Prior to introduction into the fusion chamber, the NT units are preferably gradually exposed to the fusion medium via 3 incubations containing HECM to fusion medium in ratios of 2:1, 1:2 and 0:1. Preferably, the pig cell and oocyte are electrofused in a 500 μm chamber by application of an electrical pulse of 90–120V for about 30 μsec, about 44 hours after initiation of oocyte maturation. After fusion, the resultant fused NT units are maintained in fusion medium for 5 min, then placed in HECM for 10 min, and then in NCSU 23 plus 7.5 mg/ml CB until activation. Typically activation will be effected shortly thereafter, typically less than 24 hours later, and preferably about 4–9 hours later.

The NT unit may be activated by known methods. Such methods include, e.g., culturing the NT unit at subphysiological temperature, in essence by applying a cold, or actually cool temperature shock to the NT unit. This may be most conveniently done by culturing the NT unit at room temperature, which is cold relative to the physiological temperature conditions to which embryos are normally exposed.

In a preferred embodiment, the pig NT units are activated in a 500 μm chamber by application of an electrical pulse of 30V for 30 μsec in an activation medium containing 0.28 M mannitol, 100 μM $CaCl_2$, 100 μM $MgSO_4$ and 10 mM histidine, pH 7.0. One hour later a second pulse of 15V is applied for 30 μsec. Between pulses the NT units are maintained in NCSU 23 with CB at 39° C. and 5% $CO_2$.

Alternatively, activation may be achieved by application of known activation agents. For example, penetration of oocytes by sperm during fertilization or the activation factor contained in sperm cells can activated NT units. Also, treatments such as electrical or chemical shock, calcium ionophores, and protein kinase inhibitors may be used to activate NT embryos after fusion.

Preferably, after activation the NT units are cultured for 3 to 4 hours in NCSU 23 plus CB, and thereafter in NCSU 23 without CB. The NT units can be transferred into the recipient female anytime after activation.

Alternatively, the activated NT units may then be cultured in a suitable in vitro culture medium until the generation of CICM cells and cell colonies. Culture media suitable for culturing and maturation of embryos are well known in the art. Examples of known media include Ham's F-10+10% fetal calf serum (FCS), Tissue Culture Medium-199 (TCM-199)+10% fetal calf serum, Tyrodes-Albumin-Lactate-Pyruvate (TALP), Dulbecco's Phosphate Buffered Saline (PBS), Eagle's and Whitten's media. One of the most common media used for the collection and maturation of oocytes is TCM-199, and 1 to 20% serum supplement including fetal calf serum, newborn serum, estrual cow serum, lamb, pig, or steer serum. A preferred maintenance medium includes TCM-199 with Earl salts, 10% fetal calf serum, 0.2 mM Na pyruvate and 50 μg/ml gentamicin sulphate. More preferably, the medium used is NCSU 23, and 2 to 5 days after activation the NT units are cultured in fresh NCSU 23 and 5 to 10% fetal calf serum. Any of the above may also involve co-culture with a variety of cell types such as granulosa cells, oviduct cells, BRL cells and uterine cells and STO cells.

Another maintenance medium is described in U.S. Pat. No. 5,096,822 to Rosenkrans, Jr. et al., which is incorporated herein by reference. This embryo medium, named CR1, contains the nutritional substances necessary to support an embryo.

Typically, the NT units are cultured in NCSU 23 plus 5 to 10% FCS until the NT units reach a size suitable for transferring to a recipient female, or for obtaining cells which may be used to produce CICM cells or cell colonies. Preferably, these NT units will be cultured until at least about 2 to 400 cells, more preferably about 4 to 128 cells, and most preferably at least about 50 cells. The culturing will be effected under suitable conditions, i.e., about 38.5° C. and 5% $CO_2$, with the culture medium changed in order to optimize growth typically about every 2–5 days, preferably about every 3 days.

The methods for embryo transfer and recipient animal management in the present invention are standard procedures used in the embryo transfer industry. Synchronous transfers are important for success of the present invention, i.e., the stage of the NT embryo is in synchrony with the estrus cycle of the recipient female. This advantage and how to maintain recipients are discussed in Wall et al ("Development of porcine ova that were centrifuged to permit visualization of pronuclei and nuclei," *Biol. Reprod.*, 32:645–651 (1985)), the contents of which are hereby incorporated by reference.

The present invention can also be used to clone genetically engineered or transgenic pigs. As explained above, the present invention is advantageous in that transgenic procedures can be simplified by working with a differentiated cell source that can be clonally propagated. In particular, the differentiated cells used for donor nuclei have a desired DNA sequence inserted, removed or modified. Those genetically altered, differentiated cells are then used for nuclear transplantation with enucleated oocytes.

Any known method for inserting, deleting or modifying a desired DNA sequence from a mammalian cell may be used for altering the differentiated cell to be used as the nuclear donor. These procedures may remove all or part of a DNA sequence, and the DNA sequence may be heterologous. Included is the technique of homologous recombination, which allows the insertion, deletion or modification of a DNA sequence or sequences at a specific site or sites in the cell genome.

The present invention can thus be used to provide adult pigs with desired genotypes. Multiplication of adult pigs with proven genetic superiority or other desirable traits is particularly useful, including transgenic or genetically engineered animals, and chimeric animals. Thus, the present invention will allow production of single sex offspring, and production of pigs having improved meat production, reproductive traits and disease resistance. Furthermore, cell and tissues from the NT fetus, including transgenic and/or chimeric fetuses, can be used in cell, tissue and organ transplantation for the treatment of numerous diseases as described below in connection with the use of CICM cells. Hence, transgenic pigs have uses including models for diseases, xenotransplantation of cells and organs, and production of pharmaceutical proteins.

For production of CICM cells and cell lines, after NT units of the desired size are obtained, the cells are mechanically removed from the zone and are then used. This is preferably effected by taking the clump of cells which comprise the NT unit, which typically will contain at least about 50 cells, washing such cells, and plating the cells onto a feeder layer, e.g., irradiated fibroblast cells. Typically, the cells used to obtain the stem cells or cell colonies will be obtained from the inner most portion of the cultured NT unit which is preferably at least 50 cells in size. However, NT units of smaller or greater cell numbers as well as cells from other portions of the NT unit may also be used to obtain ES cells and cell colonies. The cells are maintained in the feeder layer in a suitable growth medium, e.g., alpha MEM supplemented with 10% FCS and 0.1 mM β-mercaptoethanol (Sigma) and L-glutamine. The growth medium is changed as often as necessary to optimize growth, e.g., about every 2–3 days.

This culturing process results in the formation of CICM cells or cell lines. One skilled in the art can vary the culturing conditions as desired to optimize growth of the particular CICM cells. Also, genetically engineered or transgenic pig CICM cells may be produced according to the present invention. That is, the methods described above can be used to produce NT units in which a desired DNA sequence or sequences have been introduced, or from which all or part of an endogenous DNA sequence or sequences have been removed or modified. Those genetically engineered or transgenic NT units can then be used to produce genetically engineered or transgenic CICM cells.

The resultant CICM cells and cell lines have numerous therapeutic and diagnostic applications. Most especially, such CICM cells may be used for cell transplantation therapies.

In this regard, it is known that mouse embryonic stem (ES) cells are capable of differentiating into almost any cell type, e.g., hematopoietic stem cells. Therefore, pig CICM cells produced according to the invention should possess similar differentiation capacity. The CICM cells according to the invention will be induced to differentiate to obtain the desired cell types according to known methods. For example, the subject pig CICM cells may be induced to differentiate into hematopoietic stem cells, neural cells, muscle cells, cardiac muscle cells, liver cells, cartilage cells, epithelial cells, urinary tract cells, neural cells, etc., by culturing such cells in differentiation medium and under conditions which provide for cell differentiation. Medium and methods which result in the differentiation of CICM cells are known in the art as are suitable culturing conditions.

For example, Palacios et al, *Proc. Natl. Acad. Sci., USA*, 92:7530–7537 (1995) teaches the production of hematopoietic stem cells from an embryonic cell line by subjecting stem cells to an induction procedure comprising initially culturing aggregates of such cells in a suspension culture medium lacking retinoic acid followed by culturing in the same medium containing retinoic acid, followed by transferral of cell aggregates to a substrate which provides for cell attachment.

Moreover, Pedersen, *J. Reprod. Fertil. Dev.*, 6:543–552 (1994) is a review article which references numerous articles disclosing methods for in vitro differentiation of embryonic stem cells to produce various differentiated cell types including hematopoietic cells, muscle, cardiac muscle, nerve cells, among others.

Further, Bain et al, *Dev. Biol.*, 168:342–357 (1995) teaches in vitro differentiation of embryonic stem cells to produce neural cells which possess neuronal properties. These references are exemplary of reported methods for obtaining differentiated cells from embryonic or stem cells. These references and in particular the disclosures therein relating to methods for differentiating embryonic stem cells are incorporated by reference in their entirety herein.

Thus, using known methods and culture medium, one skilled in the art may culture the subject CICM cells, including genetically engineered or transgenic CICM cells, to obtain desired differentiated cell types, e.g., neural cells, muscle cells, hematopoietic cells, etc.

The subject CICM cells may be used to obtain any desired differentiated cell type. Therapeutic usages of such differentiated cells are unparalleled. For example, hematopoietic stem cells may be used in medical treatments requiring bone marrow transplantation. Such procedures are used to treat many diseases, e.g., late stage cancers such as ovarian cancer and leukemia, as well as diseases that compromise the immune system, such as AIDS. Hematopoietic stem cells can be obtained, e.g., by fusing adult somatic cells of a cancer or AIDS patient, e.g., epithelial cells or lymphocytes with an enucleated oocyte, obtaining CICM cells as described above, and culturing such cells under conditions which favor differentiation, until hematopoietic stem cells are obtained. Such hematopoietic cells may be used in the treatment of diseases including cancer and AIDS.

The present invention can be used to replace defective genes, e.g., defective immune system genes, or to introduce genes which result in the expression of therapeutically beneficial proteins such as growth factors, lymphokines, cytokines, enzymes, etc.

DNA sequences which may be introduced into the subject CICM cells include, by way of example, those which encode epidermal growth factor, basic fibroblast growth factor, glial derived neurotrophic growth factor, insulin-like growth factor (I and II), neurotrophin-3, neurotrophin-4/5, ciliary neurotrophic factor, AFT-1, cytokines (interleukins, interferons, colony stimulating factors, tumor necrosis factors (alpha and beta), etc.), therapeutic enzymes, etc.

The present invention includes the use of pig cells in the treatment of human diseases. Thus, pig CICM cells, NT fetuses and NT and chimeric offspring (transgenic or non-transgenic) may be used in the treatment of human disease conditions where cell, tissue or organ transplantation is warranted. In general, CICM cell, fetuses and offspring according to the present invention can be used within the same species (autologous, syngenic or allografts) or across species (xenografts). For example, brain cells from pig NT fetuses may be used to treat Parkinson's disease.

Also, the subject CICM cells, may be used as an in vitro model of differentiation, in particular for the study of genes which are involved in the regulation of early development. Also, differentiated cell tissues and organs using the subject CICM cells may be used in drug studies.

Further, the subject CICM cells may be used as nuclear donors for the production of other CICM cells and cell colonies.

In order to more clearly describe the subject invention, the following examples are provided.

EXAMPLES

Materials and Methods for Pig Cloning
Modified NCSU 37 Medium (mNCSU 37)

| Component | Mol. Wt. | Conc. (mM) | g/l |
|---|---|---|---|
| NaCl | 58.45 | 108.73 | 6.3553 |
| NaHCO$_3$ | 84.00 | 25.07 | 2.1059 |
| KCl | 74.55 | 4.78 | 0.3563 |
| KH$_2$PO$_4$ | 136.09 | 1.19 | 0.1619 |
| MgSO$_4$7H$_2$O | 246.50 | 1.19 | 0.2933 |
| CaCl$_2$2H$_2$O | 147.00 | 1.70 | 0.2499 |
| Glucose | 180.20 | 5.55 | 1.0000 |
| Glutamine | 146.10 | 1.00 | 0.1461 |
| Sorbitol | 182.20 | 12.00 | 2.1864 |
| Insulin | — | 5 mg/l | 0.0050 |
| Penicillin G | — | 100 IU/l | 0.0650 |
| Streptomycin | — | 50 mg/l | 0.0500 |

Use 18 mohm, RO, DI water.

pH should be 7.4, Check osmolarity and record.

Sterilize by vacuum filtration (0.22 μm), date and initial bottle.

Store at 4° C. and use within 10 days.

Modified TL-Hepes-PVA Medium (Hepes-PVA)

| Component | Mol. Wt. | Conc. (mM) | g/l |
|---|---|---|---|
| NaCl | 58.45 | 114.00 | 6.6633 |
| KCl | 74.55 | 3.20 | 0.2386 |
| NaHCO$_3$ | 84.00 | 2.00 | 0.1680 |
| NaH$_2$PO$_4$ | 120.00 | 0.34 | 0.0408 |
| Na Lactate** | 112.10 | 10.00 | 1.868 ml |
| MgCl$_2$6H$_2$O | 203.30 | 0.50 | 0.1017 |
| CaCl$_2$2H$_2$O* | 147.00 | 2.00 | 0.2940 |
| Sorbitol | 182.20 | 12.00 | 2.1864 |
| HEPES | 238.30 | 10.00 | 2.3830 |
| Na Pyruvate | 110.00 | 0.20 | 0.0220 |
| Gentamycin | — | — | 500 µl |
| Penicillin G | — | — | 0.0650 |
| PVA | 10,000 | — | 0.1000 |

**60% syrup
*Add CaCl$_2$2H$_2$O last, slowly to prevent precipitation

Use 18 mohm, RO, DI water.
Adjust pH to 7.4, Check osmolarity and record.
Sterilize by vacuum filtration (0.22 µm), date and initial bottle.
Store at 4° C. and use within 10 days.

NCSU 23 Medium

| Component | Mol. Wt. | Conc. (mM) | g/l |
|---|---|---|---|
| NaCl | 58.45 | 108.73 | 6.3553 |
| NaHCO$_3$ | 84.00 | 25.07 | 2.1059 |
| KCl | 74.55 | 4.78 | 0.3563 |
| KH$_2$PO$_4$ | 136.09 | 1.19 | 0.1619 |
| MgSO$_4$7H$_2$O | 246.50 | 1.19 | 0.2933 |
| CaCl$_2$2H$_2$O | 147.00 | 1.70 | 0.2499 |
| Glucose | 180.20 | 5.55 | 1.0000 |
| Glutamine | 146.10 | 1.00 | 0.1461 |
| Taurine | 125.10 | 7.00 | 0.8757 |
| Hypotaurine | 109.10 | 5.00 | 0.5455 |
| BSA | — | 0.4% | 4.0000 |
| Penicillin G | — | 100 IU/l | 0.0650 |
| Streptomycin | — | 50 mg/l | 0.0500 |

Use 18 mohm, RO, DI water.
pH should be 7.4, Check osmolarity and record.
Sterilize by vacuum filtration (0.22 µm) using red Nalgene filters, date and initial bottle.
Store at 4° C. and use within 10 days.
NOTE: BSA type is important. Preferably use Sigma BSA catalog # A-7906. Also, Pen G/Strept is optional.

Media Preparation
Maturation Medium (MAT)
18.0 ml mNCSU 37
2.0 ml porcine follicular fluid (pFF)
7.0 µl of diluted β-Mercaptoethanol (dilute 10 µl β-Mercaptoethanol to 990 µl mNCSU 37; 50 µM final concentration)
0.002 g cysteine (0.6 mM final concentration)
20 µl EGF Stock (Epidermal Growth Factor from 10 ng/µl EGF stock)
Filter through 0.22 µm into 10 ml culture tubes. Label with date and initials, equilibrate in CO$_2$ incubator.

Porcine Follicular Fluid Preparation
Collect follicular fluid from 3–6 mm follicles of prepubertal gilts and allow oocytes and follicular cells to settle for 5–10 minutes. Aspirate the pFF and move to 15 ml conical tubes. Centrifuge on Sorvall at 4° C. at 3000 rpm for 30 minutes. Remove tubes, collect pFF above pellet, pool and filter through a 0.8 µm, then a 0.45 µm filter (Sterivex). Aliquot to 1.5 ml sterile microfuge tubes and freeze at −20° C. until use.

Epidermal Growth Factor Stock (EGF)
100 µg EGF
10 ml mNCSU 37 with 0.1% BSA
Mix well. Aliquot to 25 µl, freeze at −20° C.

Equine Chorionic Gonadotropin and Human Chorionic Gonadotropin Stock for MAT (PMSG/hCG)
ECG (PMSG 6000; Intervet Inc., Millsboro; DE 19966) Dilute 6000 IU to 2000 IU/ml by adding 3 ml dH$_2$O.
hCG (Chorulon; Intervet Inc.) Dilute 10,000 IU to 2000 IU/ml by adding 5 ml dH$_2$O.
Mix 1 ml PMSG and 1 ml hCG to get 1000 IU/ml of each hormone. Make 50 µl aliquots and freeze at −20° C. Freeze remaining PMSG and hCG stocks as well.

db-cAMP 100 mM Stock
25 mg db-cAMP (stored in dessicator at −20° C.)
0.509 ml dH$_2$O
Mix well. Make 50 µl aliquots and freeze at −20° C.

Fusion Medium
0.28 M Mannitol
10 µM CaCl$_2$
100 µM MgSO$_4$
10 mM Histidine
adjust to pH 7.0

Activation Medium
0.28 M Mannitol
100 µM CaCl$_2$
100 µM MgSO$_4$
10 mM Histidine
adjust to pH 7.0

Antibiotic/Antimycotic (Ab/Am)
100 U/l Penicillin, 100 µg/l streptomycin and 0.25 µg/l amphotericin B, (Gibco #15240-062)
Add a 10 ml aliquot to each liter of saline.
Add 10 µl to each ml of semen.

Oocyte-Cumulus Complex (OCC) Collection
Ovaries are transported to the lab at 25° C. and immediately washed with 0.9% saline with antibiotic/antimycotic (10 ml/L; Gibco #600-5240 g). Follicles between 3–6 mm are aspirated using 18 g needles and 50 ml Falcon tubes connected to vacuum system (GEML bovine system). After tube is filled, OCC's are allowed to settle for 5–10 minutes. Follicular fluid (pFF) is aspirated and saved for use in culture system if needed (see pFF preparation protocol below).

OCC Washing
OCCs are resuspended in 20 ml Hepes-PVA and allowed to settle; repeat 2 times. After last wash, OCCs are moved to grid dishes and selected for culture. Selected OCCs are washed twice in 60 mm dishes of Hepes-PVA. All aspiration and oocyte recovery are performed at room temperature (approx. 25° C.).

In vitro Maturation (IVM)
After washing 3 times in MAT, 50 OCCs are moved to 0.5 ml of MAT in 4 well Nunc plate (inner compartment contains 1–2 ml MAT or mNCSI 37). Add 5 µl of 100 mM db-cAMP (in water) to each well of OCC. Culture 22 hours with hormones. Wash 3 times with fresh MAT without hormones and move to 0.5 ml wells of fresh MAT, approximately 50 oocytes/well. Incubate for 22 hours at 39° C. in 5.0% CO$_2$ atmosphere for a total of approximately 40 hours in MAT.

Isolation of Primary Cultures of Porcine Embryonic and Adult Fibroblast Cells

Primary cultures of porcine fibroblasts are obtained from pig fetuses 30 to 114 days postfertilization, preferably 35 days. The head, liver, heart and alimentary tract are aseptically removed, the fetuses minced and incubated for 30 minutes at 37° C. in prewarmed trypsin EDTA solution (0.05% trypsin/0.02% EDTA; GIBCO, Grand Island, N.Y.). Fibroblast cells are plated in tissue culture dishes and cultured in fibroblast growth medium (FGM) containing: alpha-MEM medium (BioWhittaker, Walkersville, Md.) supplemented with 106 fetal calf serum (FCS) (Hyclone, Logen, Utah), penicillin (100 IU/ml) and streptomycin (50 $\mu$l/ml). The fibroblasts are grown and maintained in a humidified atmosphere with 5% $CO_2$ in air at 37° C.

Adult fibroblast cells are isolated from the lung and skin of a pig. Minced lung tissue is incubated overnight at 10° C. in trypsin EDTA solution (0.05% trypsin/0.02% EDTA; GIBCO, Grand Island, N.Y.). The following day tissue and any disassociated cells are incubated for one hour at 37° C. in prewarmed trypsin EDTA solution (0.05% trypsin/0.02% EDTA; GIBCO, Grand Island, N.Y.) and processed through three consecutive washes and trypsin incubations (one hr). Fibroblast cells are plated in tissue culture dishes and cultured in alpha-MEM medium (BioWhittaker, Walkersville, Md.) supplemented with 10% fetal calf serum (FCS) (Hyclone, Logen, Utah), penicillin (100 IU/ml) and streptomycin (50 $\mu$l/ml). The fibroblast cells can be isolated at virtually any time in development, ranging from approximately post embryonic disc stage through adult life of the animal (porcine day 9 to 10 after fertilization to 5 years of age or longer).

Preparation of Fibroblast Cells for Nuclear Transfer

Examples of fetal fibroblasts which may be used as donor nuclei are:

1. Proliferating fibroblast cells that are not synchronized in any one cell stage or serum starved or quiescent can serve as nuclear donors. The cells from the above culture are treated for 10 minutes with trypsin EDTA and are washed three times in 100% fetal calf serum. Single cell fibroblast cells are then placed in micromanipulation drops of HbT medium (Bavister et al., 1983). This is done 10 to 30 min prior to transfer of the fibroblast cells into the enucleated pig oocyte. Preferably, proliferating transgenic fibroblast cells having the CMV promoter and green fluorescent protein gene (9th passage) are used to produce NT units.

2. By a second method, fibroblast cells are synchronized in G1 or G0 of the cell cycle. The fibroblast cells are grown to confluence. Then the concentration of fetal calf serum in the FGM is cut in half over four consecutive days (day 0=10%, day 1=5%, day 2-2.5%, day 3=1.25%, day 4=0.625%. On the fifth day the cells are treated for 10 minutes with trypsin EDTA and washed three times in 100% fetal calf serum. Single cell fibroblasts are then placed in micromanipulation drops of HbT medium. This is done within 15 min prior to transfer of the fibroblast cells into the enucleated pig oocyte.

Removal of Cumulus Cells

After a maturation period, which ranges from about 30 to 50 hours, and preferably about 40 hours, the oocytes will be enucleated. Prior to enucleation the oocytes will preferably be removed and placed in HECM (Seshagiri and Bavister, 1989) containing 1 milligram per milliliter of hyaluronidase prior to removal of cumulus cells. This may be effected by repeated pipetting through very fine bore pipettes or by vortexing briefly (about 3 minutes). The stripped oocytes are then screened for polar bodies, and the selected metaphase II oocytes, as determined by the presence of polar bodies, are then used for nuclear transfer. Enucleation follows.

Enucleation, Transfer of Fibroblast Cells and Fusion

The cumulus free pig oocytes are enucleated with a beveled micropipette at approximately 40 hrs post maturation (hpm). This procedure has been described previously by Prather et al., 1989, the contents of which are hereby incorporated by reference. The oocytes are enucleated in HECM HEPES and 7.5 mg/ml CB plus 0.15 M sucrose. Enucleation is confirmed after the oocytes have been incubated for greater than 20 minutes in NCSU 23 medium plus Hoechst 3342 (3 $\mu$g/ml; Sigma). Individual donor cells (fibroblasts) are then placed in the perivitelline space of the recipient oocyte using the beveled micropipette in HECM HEPES plus 0.15 M sucrose and CB (7.5 mg/ml). The porcine oocyte cytoplasm and the donor nucleus (NT unit) are fused together using electrofusion techniques. The NT units are washed three times in increasing amounts of fusion medium (ratio of HECM HEPES to fusion medium of 2:1, 1:2 and 0:1). The fusion chamber consists of two wires of 200 $\mu$m in diameter running in parallel with a gap of 500 $\mu$m. Each NT unit is manually aligned so that the membranes to be fused are parallel to the two wires. One fusion pulse consisting of 100 V for 30 $\mu$sec is applied to the NT units in an electrofusion chamber. This occurs at 44 to 45 hpm. NT units are incubated in fusion medium for 5 min and then in HECM HEPES for 10 min. The NT units are placed back into NCSU 23 plus CB medium until 47 to 49 hpm.

Activation

Examples of methods of activation which may be used at 47 to 49 hrs post activation are:

1. Single activation pulse. NT units are removed from the NCSU 23 plus CB and washed three times in activation medium. After equilibration, the NT units are placed into the fusion chamber (500 $\mu$m gap) filled with activation medium as described in the fusion procedure. A pulse of 30 V for 30 $\mu$sec is applied. Then the NT units are immediately washed three times in HECM HEPES and cultured (39° C., 5% $CO_2$) in NCSU 23 for 2 more hours until embryo transfer or in vitro culture (39° C., 5% $CO_2$ in NCSU 23). If cultured, NT units are placed in fresh NCSU 23 plus 5% fetal calf serum on day 2 of culture. The results in Table 1 indicate that oocytes can be activated using this procedure and that they have developmental capabilities.

2. Two activation pulses. NT units are removed from the NCSU 23 plus CB and washed three times in activation medium. After equilibration the NT units are placed back into the fusion chamber (500 $\mu$m gap) filled with activation medium as described in the fusion procedure. A pulse of 30 V for 30 $\mu$sec is applied. Then the NT units are immediately washed three times in HECM HEPES, placed back in NCSU 23 plus CB, and cultured in this at 39° C., 5% $CO_2$, until the next electrical pulse 1 hr later. After 1 hr this time the activation medium equilibration step is repeated and a pulse of 15 V for 30 $\mu$sec is applied. Then the NT units are immediately washed three times in HECM HEPES, placed back in NCSU 23 plus CB, and cultured in this medium at 39° C., 5% $CO_2$, for 2 to 6 more hours. The NT units are then cultured using the same procedure described above in 1. The results in Table 1 indicate that oocytes can be activated using this procedure and that they have developmental capabilities. The same is true for nuclear transfer embryos. Four blastocyst stage NT units were produced with the two pulse activation procedure.

3. Sperm factor. First described in mammalian sperm by Stice and Robl (*Mol. Reprod. Dev.*, 25:272–280 (1990)) (the contents of which are hereby incorporated by reference), this factor causes activation in oocytes. The method of sperm factor isolation from pig sperm cells and microinjection is described in Fissore et al. (*Mol. Reprod. Dev.*, 46:176–189 (1997)), the contents of which are hereby incorporated by reference. NT units are removed from the NCSU 23 plus CB and placed in micromanipulation plates described above for enucleation and fibroblast transfer. Using a micro-injection needle (1 μm opening) filled with sperm factor the oocytes undergo activation after the delivery of the factor into the cytoplasm of the NT unit. After microinjection, the NT embryos are washed in HECM HEPES and held in NCSU 23 plus CB for 2 to 6 hours, and therafter in NCSU 23 until embryo transfer.

TABLE 1

Development of activated oocytes and NT units using different activation procedures.

| | number given activation stimulus | number cleaved (began to develop) [%] | number to blastocyst stage (eight day old embryos) [%] |
|---|---|---|---|
| Single pulse oocytes | 52 | 6[12] | 1[2] |
| Double pulse oocytes | 85 | 8[10] | 3[4] |
| Double pulse NT units | 55 | 10[18] | 4[7] |
| Sperm-factor oocytes | 49 | 4[8] | 2[4] |

Embryo Transfer

Methods of embryo one cell embryo transfer in pigs are well known (see, for example, Pinkert et al., 1993, the contents of which are hereby incorporated by reference). Briefly, 20 to 30 NT units are synchronously transferred into the oviduct of bred or unbred gilts. After and beyond 29 days of gestation, nuclear transfer fetuses (transgenic or non-transgenic) can be recovered from the recipient gilt. Alternatively, the fetuses are allowed to go to term (114 day gestation) and cloned pig offspring are produced.

What is claimed is:

1. A method of cloning a pig, comprising:
   (i) inserting a non-quiescent differentiated pig cell or non-quiescent differentiated pig cell nucleus into an enucleated pig oocyte, under conditions suitable for the formation of a nuclear transfer (NT) unit;
   (ii) activating the resultant NT unit; and
   (iii) transferring said activated NT unit to a host pig such that the NT unit develops into a fetus.

2. The method according to claim 1, which further comprises developing the fetus to an offspring.

3. The method according to claim 1, wherein a desired DNA is inserted, removed or modified in said differentiated pig cell or differentiated pig cell nucleus, thereby resulting in the production of a genetically altered NT unit.

4. The method according to claim 3, which further comprises developing the fetus to an offspring.

5. The method according to claim 1, which comprises culturing said activated nuclear transfer unit until greater than the 2-cell developmental stage.

6. The method according to claim 1, wherein the differentiated pig cell or differentiated pig cell nucleus is derived from mesoderm.

7. The method according to claim 1, wherein the differentiated pig cell or differentiated pig cell nucleus is derived from ectoderm.

8. The method according to claim 1, wherein the differentiated pig cell or differentiated pig cell nucleus is derived from endoderm.

9. The method according to claim 1, wherein the differentiated pig cell or differentiated pig cell nucleus is a fibroblast cell or cell nucleus.

10. The method according to claim 1, wherein the differentiated pig cell or differentiated pig cell nucleus is an adult cell or adult cell nucleus.

11. The method according to claim 1, wherein the differentiated pig cell is a fetal cell or differentiated pig cell nucleus is isolated from a fetal cell.

12. The method according to claim 1, wherein the enucleated oocyte is matured prior to enucleation.

13. The method according to claim 1, wherein the nuclear transfer unit is activated by exposure to two electrical pulses.

14. The method according to claim 1, wherein the nuclear transfer unit is activated by exposure to a single electrical pulse.

15. The method according to claim 1, wherein the nuclear transfer unit is activated by exposure to at least one activating factor isolated from sperm cells.

16. The method according to claim 3, wherein microinjection is used to insert a heterologous DNA.

17. The method according to claim 3, wherein electroporation is used to insert a heterologous DNA.

18. The method according to claim 5, which further comprises combining a cell of the NT unit with an embryo to produce a chimeric embryo, which is then transferred to a host pig such that the chimeric embryo develops into a chimeric fetus.

19. The method according to claim 18, which further comprises developing the fetus to an offspring.

20. The method according to claim 1 wherein said non-quiescent differentiated pig cell has been expanded in culture or said non-quiescent differentiated pig cell nucleus is isolated from non-quiescent differentiated pig cell that has been expanded in culture.

21. A method of cloning a pig, comprising:
   (i) inserting a non-quiescent differentiated pig CICM cell or non-quiescent differentiated pig CICM cell nucleus into an enucleated pig oocyte, under conditions suitable for the formation of a nuclear transfer (NT) unit;
   (ii) activating the resultant NT unit; and
   (iii) transferring said activated NT unit to a host pig such that the NT unit develops into a fetus.

22. The method according to claim 21, which comprises culturing said activated nuclear transfer unit until greater than the 2-cell developmental stage.

23. The method according to claim 21, which further comprises developing the fetus to an offspring.

24. A method of producing a non-human mammalian embryo by nuclear transfer comprising transplantation of a non-human mammalian cell or a nucleus of a non-human mammalian cell into an enucleated oocyte of the same species as the donor cell or donor cell nucleus, activation of the recipient oocyte containing the donor cell or donor cell nucleus, and incubation of the activated oocyte to produce an embryo, wherein the donor cell is a non-quiescent mammalian differentiated cell or wherein the donor nucleus is from a non-quiescent mammalian differentiated cell.

25. The method according to claim 1 wherein said non-human mammalian embryo is porcine.

26. The method according to claim 1 wherein said non-human mammalian embryo is an ungulate.

* * * * *